United States Patent [19]

Erickson

[11] Patent Number: 4,573,917
[45] Date of Patent: Mar. 4, 1986

[54] MEASURING DEVICE FOR MAXILLOFACIAL TRIAL SURGERY

[76] Inventor: Kim L. Erickson, 36 Lawrence Ave., Bedford Hills, N.Y. 10507

[21] Appl. No.: 681,371

[22] Filed: Dec. 13, 1984

[51] Int. Cl.$^4$ .............................................. A61C 3/00
[52] U.S. Cl. ........................................ 433/75; 433/56; 433/60; 433/72
[58] Field of Search ..................... 433/75, 72, 60, 54, 433/55, 56, 57, 50; 33/174 D

[56] References Cited

U.S. PATENT DOCUMENTS

| | | | |
|---|---|---|---|
| 1,526,619 | 2/1925 | Williams | 33/174 D |
| 2,528,053 | 10/1950 | Harris | 433/75 |
| 2,545,249 | 3/1951 | Ackerman | 33/174 D |
| 2,616,176 | 11/1952 | Rodin | 33/174 D |
| 3,067,515 | 12/1962 | Wilkinson | 433/60 |
| 3,123,914 | 3/1964 | De Pietro | 433/60 |
| 3,344,525 | 10/1967 | Harris | 433/50 |
| 3,439,421 | 4/1969 | Perkowski | 433/56 |
| 4,189,835 | 2/1980 | Seldin | 433/55 |
| 4,445,855 | 5/1984 | Hobo et al. | 433/56 |

*Primary Examiner*—John J. Wilson
*Attorney, Agent, or Firm*—Alfred E. Miller

[57] ABSTRACT

A measuring device for use in model surgery in connection with the surgical treatment of the teeth and jaws, commonly referred to as orthognathic surgery. The trial surgery is performed on a plaster dental model which has been correctly mounted on a dental articulator, and in which the Frankfort Horizontal plane or axis orbital plane is utilized. In addition, a model block to which the dental model is affixed is placed on a model platform provided with a caliper, such as an electronic digital caliper, precisely mounted relative to the base of the platform so that measurements of the dental models are made which are free from error due to positioning relative to the base line, as well as due to parallax.

12 Claims, 18 Drawing Figures

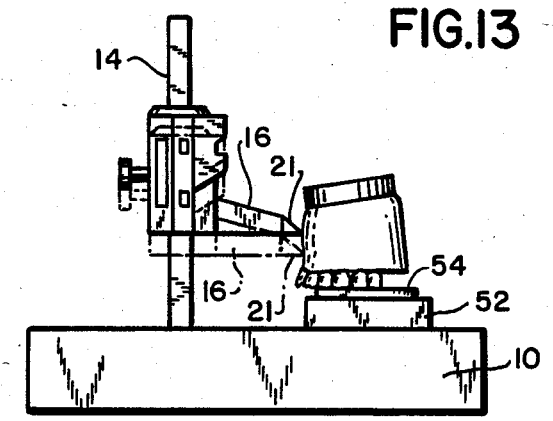
FIG. 13
FIG. 11
FIG. 12
FIG. 6
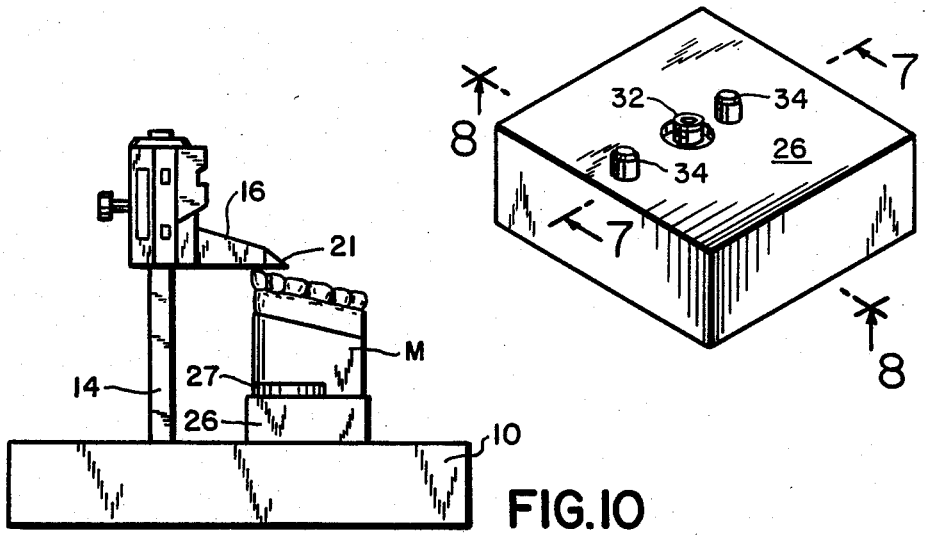
FIG. 10

FIG.18
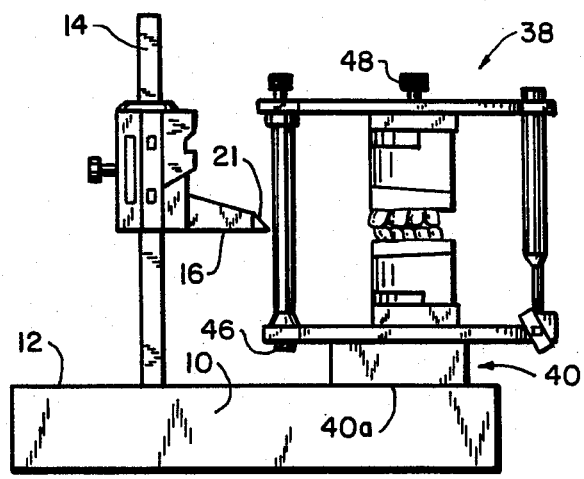
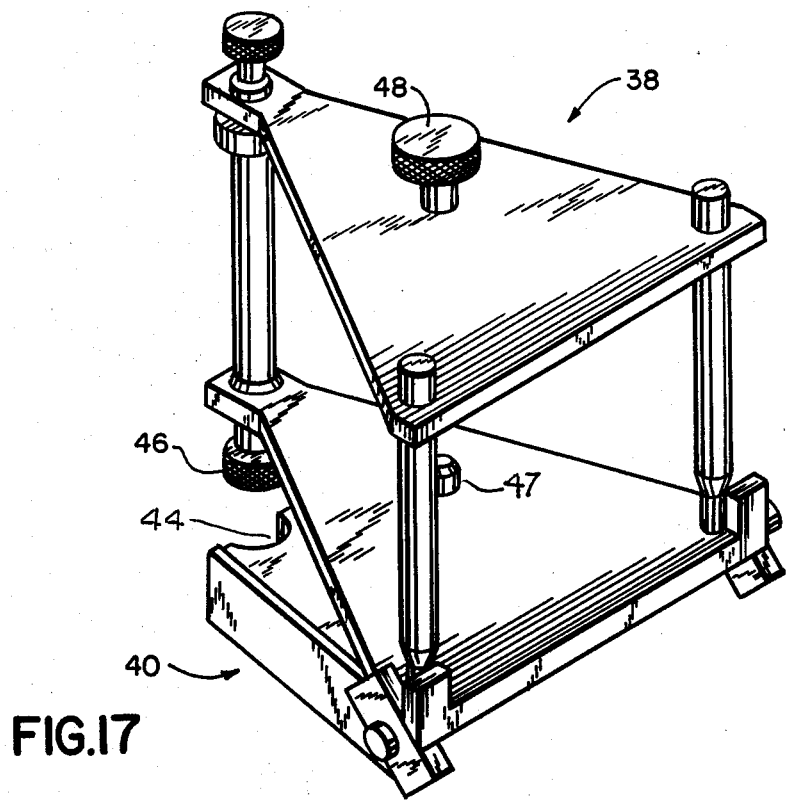
FIG.17

MEASURING DEVICE FOR MAXILLOFACIAL TRIAL SURGERY

The present invention relates to a measuring device for use in the surgical treatment of dento-facial growth deformities, and more commonly referred to as surgery of the teeth and jaws. This type of surgery may also be referred to as orthognathic surgery, maxillofacial surgery, reconstructive jaw surgery or surgical orthodontics. In addition, the present measuring device may be used in cranio-facial surgery, or in the evaluation of more routine orthodontic procedures.

In preparation for the aforesaid types of surgery, the surgeon performs what is commonly called "model surgery". This trial surgery is performed on plaster dental models which have been correctly mounted or placed on a dental articulator. The latter is a mechanical jaw device which can simulate the functional movements of the lower jaw, or mandible, against the upper jaw, or maxilla.

The prior art method of making measurements for trial surgery involved the use of a hand-held millimeter ruler as set forth in the article by Dr. Tom Hohl entitled "Model Surgery" in a text book entitled Surgical Correction of Dento-facial Deformities by Dr. William H. Bell et al, and published in 1980. The hand-held millimeter ruler is a standard type of measuring device presently used by a large majority of surgeons. It should be apparent that this hand-held device is prone to many types of error. Since it is only held by hand, there may be measurement error due to an incorrect positioning of the ruler to the defined reference plane or baseline. Furthermore, inasmuch as it is hand-held it cannot be easily replaced to the exact position of the previous comparative measurement and therefore lacks satisfactory reproducibility. Moreover, since the measurements are made from a ruler that is read by eye from the measurement lines on the ruler against the object to be measured, it is prone to error due to viewing perspective or parallax.

Furthermore, Dr. Hohl's technique has a serious drawback in that the reference plane or baseline from which he bases his measurements is the occlusal plane, which is the biting surfaces of the teeth that are extremely variable and difficult to reproduce. This is so because the occlusal plane is not only difficult to accurately define but is often part of the patient's physical problem, and therefore is frequently surgically changed as part of the treatment. On the other hand, applicant's method and arrangement uses as a reference plane the Frankfort Horizontal, which is more easily defined and reproducible and universally understood by practitioners in the field. The Frankfort Horizontal is the baseline plane to which dental models are positioned when they are mounted in anatomical relationship on a dental articulator of a known type. the Frankfort Horizontal also is a defined baseline plane which is anatomically superior to the level of the surgery, and is thus not affected as a baseline by the surgery. Thus, applicant's method utilizes a different arrangement than the hand-held ruler, which is prone to errors and lacking in accuracy, and uses a reference plane which is more easily defined and reproducible.

Briefly stated, applicant's device and system permits the surgeon to make measurements in all three planes of space from dental models mounted on a dental articulator. The present model measuring device permits accurate and rapid measurements which are reproducible and free of error due to parallax or positioning relative to the reference plane. The applicant's device and system also permits the accurate and rapid marking or scribing of secondary reference lines on orthognathic surgery models prior to model surgery, thus ensuring a more accurate measurement of trial surgical movements.

It is an object of the present invention to provide a caliper, such as an electronic digital caliper, having a high order of accuracy which is precisely mounted relative to the base of a platform so that measurements of the dental models are made which are free from error due to positioning relative to the baseline, as well as due to parallax.

Another object of the present invention is to provide a specially constructed caliper having a sharp point which acts as a scribe to draw accurate parallel lines on the dental models in order to facilitate measurements. These accurately placed secondary reference lines on the mounted models as a result of the above-described method allows determination of the three-dimensional movements of the model or segments of the model.

It is important to note that pre-operative model surgery is essential in the treatment planning of dento-facial or orthognathic surgery. Thus, during a patient's pre-surgical examination, dental models of the patient are positioned anatomically within a dental articulator. The dental articulator is a known device which is a mechanical jaw device that can simulate the functional movements of the lower jaw, or mandible, against the upper jaw, or maxilla. A facebow, also a known article, is utilized in the present arrangement and is a device which is used in conjunction with a dental articulator. The facebow is used to correctly register the anatomic relationship of a patient's upper jaw to the patient's skull, and is placed at three stable points on the skull forming a plane which is very close to that patient's Frankfort Horizontal plane. That plane is defined as the upper portion of the external ear canals and the inferior bony rim of the eye. The facebow then is used to transfer the above relationship of the upper jaw to the skull, as oriented to the Frankfort Horizontal plane, to the dental articulator, thus simulating the patient's own anatomic characteristics on the articulator. With the use of the facebow, the patient's plaster model of the upper jaw is mounted on the articulator. The patient's plaster model of the lower jaw is mounted on the articulator according to the anatomic relationship between the jaws as it is found on the patient. Thus, the Frankfort horizontal plane is common to the patient and to the articulator. Consequently, due to the use of the Frankfort Horizontal plane, any point on the maxillary or mandibular models can be measured or defined in three planes of space. These measurements are recorded prior to trial surgery and then again after trial surgery. The difference between the measurements results in understanding of the net changes or movements in any given plane (vertical, horizontal and anterior-posterior).

It is a further object of the present invention to provide an accurate measuring device for orthognathic surgery which includes a model block and model platform.

It is further object of the present invention to provide another orientation block in the form of an articulator block which is used to measure vertical measurements for trial surgery on isolated surgery of the upper jaw, and can be used with the present model platform and measuring device. A further object of the present invention is to provide an occlusal block which also can be used with the present model platform and measuring device.

In order that the invention will be more clearly understood, it will now be disclosed in greater detail with reference to the accompanying drawings, in which:

FIG. 6 is a perspective view of the model block having precise surfaces and provided with locating pins and a screw connection.

FIG. 10 is a side elevational view of my model platform, model block and measuring caliper in its mounted and assembled form.

FIG. 11 is a perspective view of an occlusal block.

FIG. 12 is a perspective view of the occlusal block as seen in FIG. 11 with a dental compound material thereon.

FIG. 13 is a side elevational view of the occlusal block mounted on said model platform and having a caliper measuring device.

FIG. 17 is a perspective view of an articulator mounted in an inverted position on an articulator mounting block and FIG. 18 is a side elevational view of the assembly having the articulator mounted on the articulator block, with dental models for correct orientation, and provided with a caliper measuring device.

Figure 1:
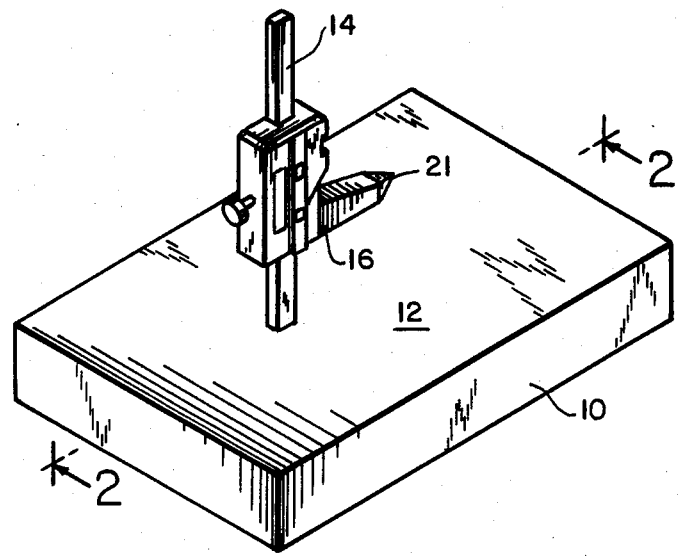
FIG. 1 is a perspective view of the model platform with a digital caliper and an adjustable scribing device constructed in accordance with the teachings of my invention.
Figure 2:
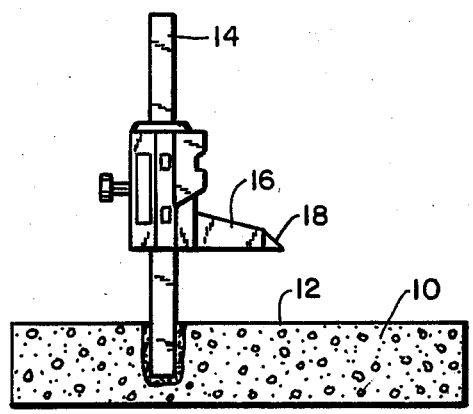
FIG. 2 is a sectional view taken along the lines 2—2 of FIG. 1.

FIGS. 1 and 2 show a model platform 10 which is generally rectangular in shape and is provided with a flat surface 12 having a tolerance of at least 0.01 millimeters. Thus, the flat surface functions effectively as a measuring surface which will be more fully explained hereinafter. As seen in FIG. 2, an accurate caliper measuring device 14 is mounted, which in the present case, is an electronic digital caliper that is accurate to 0.01 mm. It will be observed that a caliper is implanted in the model platform of the base member at precisely 90 degrees to said base, consequently the measurements taken from the base will be extremely accurate and free from error due to parallax. The caliper 14 is provided with a vertical movable arm 16 having a tip 18 that is sharpened, and is used to scribe lines on plaster dental models. The arm 16 is also provided with an opening or jack 16A for connecting a printer cable 17 to an output printer 19. Thus, the caliper has a dual function of both measuring and scribing the dental models. It should be clear that the caliper is mounted along the long axis of the model platform in a precision base member having a precision flat surface, the caliper being implanted precisely at right angles to the model platform. It is therefore used to make measurements and to scribe lines on articulator mounted dental models.

Figure 3:
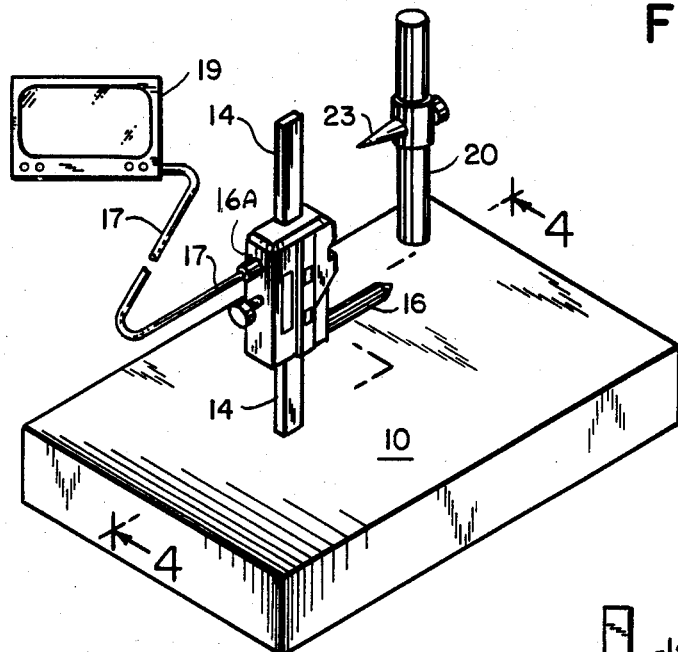
FIG. 3 is a perspective view of the model platform having a digital caliper and a separate, adjustable scriber.
Figure 4:
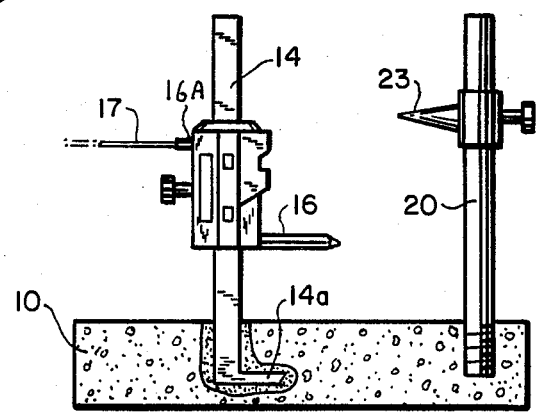
FIG. 4 is a sectional view taken along the lines 4—4 of FIG. 3.
Figure 5:
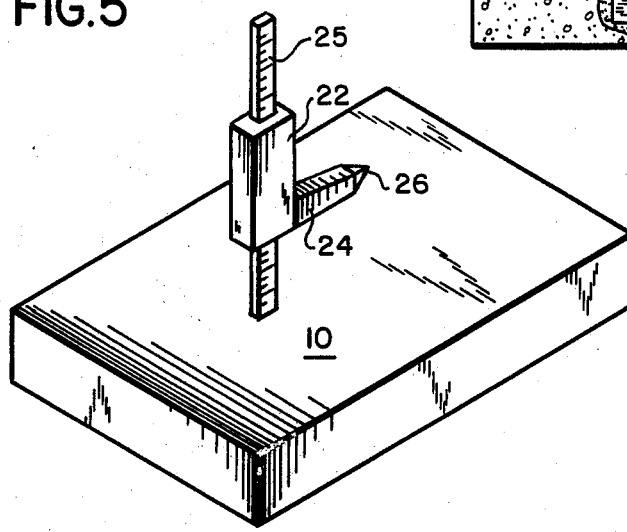
FIG. 5 is a perspective view of the model platform having another type of caliper.

As seen in FIGS. 3 and 4, the model block arrangements may take the form of a type of measuring device in which the electronic digital caliper is separate from an adjustable scribing device 20, having a carbide steel scribing tip. The caliper is provided with a pointed marker 21 for marking the dental model, while the pointed scriber 23 of scribing device 20 can be used to draw the lines on the dental model. As seen in FIG. 4, the caliper is L-shaped, having a foot portion 14a which is embedded in the platform 10 for additionally strengthening the assembly. In FIG. 5, the caliper shown therein is of a separate form of the known type, and does not provide a digital read-out. However, the caliper has a vertically extending scale 25 and the arm 24 is provided with a sharpened scribe member 26, for both measuring and marking the dental model cast.

Figure 8:
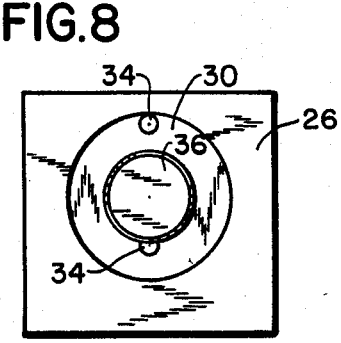
FIG. 8 is a bottom plan view of the model block.
Figure 7:
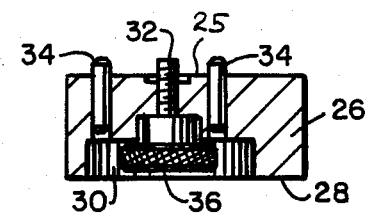
FIG. 7 is sectional view taken along the lines 7—7 of FIG. 6.
Figure 14:
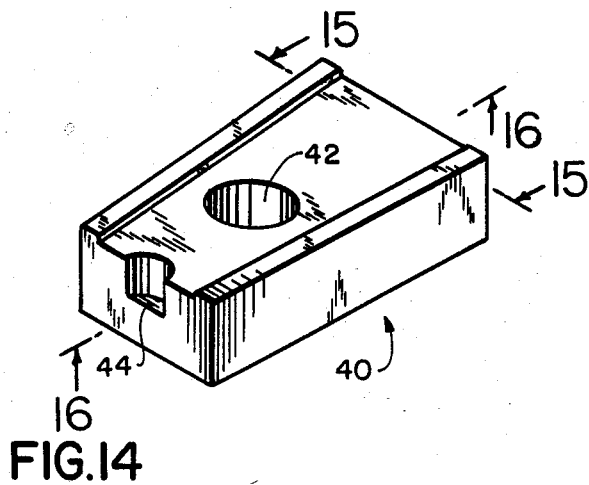
FIG. 14 is a perspective view of an articulator mounting block.
Figure 9:
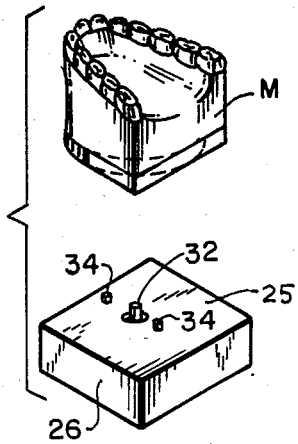
FIG. 9 is an exploded view showing the model block and the dental model about to be mounted thereon.

FIG. 6 is a perspective view of the model block, which is an important part of the present device. The model block 26 is fabricated so that all corners are exactly 90 degrees. The dimensions of the block are important in that they are very workable in the present arrangement. Furthermore, the block is responsible for orienting the plaster dental models to the flat platform. Consequently, it is the ability of the model block to orient the dental cast before and after the model surgery is performed that results in meaningful, accurate measurements and reproducible results. Thus, it should be noted that all corners of the block are exactly 90 degrees to each other, and the block is also important in that it shares the same pin indexing system as the articulator shown in FIGS. 17 and 18. Thus, the screw 32 and the locating pins 34 which hold the mounting ring to the block are oriented along the mid-line, or along axis of the block. As seen in FIGS. 7 and 8, the model block 26 is provided with a top surface 25, as well as a recess 30 in the bottom surface 28 thereof. A knurled knob 36 is located in the recess 30 and is fixed to the bottom end of screw 32 for screw-connecting the latter element in a screw-threaded hole (not shown) in mounting ring 27, as seen in FIG. 10.

The model block 26, as stated herein before, orients the plaster dental models M relative to the flat model platform 10. Furthermore, it should be noted that the dental models for pre-surgical analysis are mounted relative to the Frankfort Horizontal, and have a certain three dimensional relationship to the dental articulator, which is a reproduction of the patient's own anatomic characteristics. Therefore, when the dental model is removed from the articulator 38 and screwed on to the model block, this relationship is maintained.

As seen in FIG. 10, the model block 26, with the dental plaster cast M thereon is placed on the model platform 10 whereby vertical measurements of any point on the plaster cast can be made. These measurements have meaning only after the model surgery has been performed and a repeat measurement of the same points are made. Consequently, net changes in any dimension can be detected. When the model block 26 is placed on the right or left side relative to the mounted model, transverse measurements can be made. Furthermore, when the model block 26 is placed on end, anterior - posterior plane measurements can be made.

Figure 15:
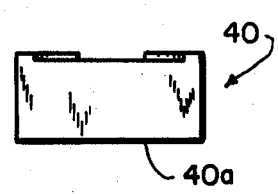
FIG. 15 is end elevational view of the mounting block shown in FIG. 14.
Figure 16:
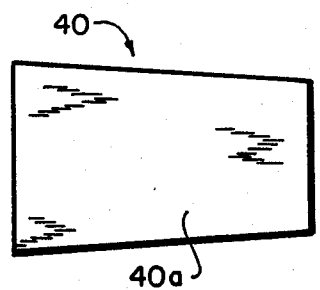
FIG. 16 is a bottom plan view of the articulator mounting block.

Prior to use of the dental articulator, of the type shown in FIGS. 17 and 18, the patient, during pre-surgical examination, is fitted with a facebow which is placed at three stable points on the skull to provide a "registration" for transfer to the dental articulator 38. The dental model which is then made from the patient is mounted on the articulator creating a virtual duplication of the patient's upper jaw in the correct vertical, horizontal and anterior-posterior position as related to the patient's skull, and having a mounting ring 27 which can then be placed upon the model block 26. Thus, a correct reference plane for mounting the dental model is established. Referring to FIGS. 14-18, an articulator, as seen in FIG. 17, is referred to generally by the reference numeral 38 and is mounted on an articulator block, referred to generally by the reference numeral 40. The articulator block 40 holds or cradles the dental articulator 38 in an inverted position against the base of the model platform 10, as seen in FIGS. 17 and 18, and forms a stable reference platform for measuring dental models. It is evident that this position maintains the Frankfort Horizontal plane parallel to the base of the model platform while the articulator is placed in a closed position. In this connection, it should be noted that the articulator block 40 is provided with recesses 42 and 44 which are designed to accept protruding knurled screw knobs, such as knobs 46 and 47 of the articulator. The knob 48 mounts the dental model's lower jaw portion on the articulator while the knob 47 mounts the dental model's upper jaw portion on the articulator in a similar fashion. Preliminarily, it should be noted that the bottom 40A of the articulator block is flat as seen in FIGS. 15 and 16, so that it can rest on the precision top surface 12 of the model platform 10.

A further additional block which may be used with the present arrangement, as seen FIGS. 11-13, is an occlusal block 52. This block may be used for a single purpose, that is when it is useful to make measurements from the occlusal plane, which is the patient's biting plane. The occlusal block 52 has approximately the same dimensions as the model block 26. However, on the top of the flat occlusal block 52 a hard wax material, referred to as a dental compound 54, is placed. The dental compound material 54 softens with heat and the teeth of the dental model are placed on it. When this dental compound hardens it functions as an interface to orient in a reproducible fashion a given dental model to the model platform, as relates to the occlusal plane. Thus, certain isolated, segmental surgical procedures performed on dental models can be measured as they relates to the occlusal or biting plane. However, this is not generally true for most of the common surgical procedures.

It should be emphasized that the articulator block and occlusal block measure only from their flat base, while the model block measures from the flat base, as well as any of the four sides thereof. Thus, as stated hereinbefore, all angles must be exactly 90 degrees with the model block 26, so that measurements from the sides can be made. On the other hand, the other above-described blocks do not have to be precise on all four sides, but must be perfectly flat with the top surface being parallel to the bottom of the blocks.

The present arrangement solves the problems inherent in prior arrangements and methods for making measurements relative to model surgery. By using the Frankfort Horizontal or the axis orbital plane as a reference plane, and by using an accurate caliper mounted 90 degrees to a flat base, this arrangement improves the degree of accuracy and removes errors to the positioning of the ruler and parallax. In addition, the caliper's sharp point acts to scribe and to draw accurate parallel lines on the models to facilitate measurements. Thus, by improving the degree of accuracy and by removing errors due to measurement techniques, the model platform and orientation blocks can be used to accurately measure jaw and jaw segment movements during the trial or model surgery. These measurements give the surgeon valuable and accurate quantative information in three planes of space that facilitates the actual surgery when performed on a patient.

What I claim is:

1. A measuring device for orthognathic surgery utilizing the Frankfort Horizontal reference plane and for use in surgical planning comprising a model platform having a precisely flat platform surface representing the Frankfort Horizontal plane, a model block resting on said platform surface and provided with a dental model thereon that has been oriented relative to said model platform, a vertically movable caliper mounted on and 90 degrees to said platform and having means for accurately measuring said dental model, and a scriber maintained substantially parallel to said flat platform surface for accurately placing reference lines that have been measured by said caliper on said mounted dental model for facilitating prospective surgical procedures.

2. A measuring device as claimed in claim 1 wherein said model block is rectangular-shaped and is provided with precisely flat top and bottom surfaces, and in which all corners are 90 degrees.

3. A measuring device as claimed in claim 1 wherein said flat platform top surface has a tolerance of at least 0.01 millimeter.

4. A measuring device as claimed in claim 1 wherein said caliper is an electronic digital caliper.

5. A measuring device as claimed in claim 1 wherein said caliper is L-shaped having a vertically extending leg relative to the flat platform top surface, and a foot embedded in said platform.

6. A measuring device as claimed in claim 1 wherein said scriber is separately mounted on said flat platform from said caliper, and is adjustably movable in a vertical plane.

7. A measuring device as claimed in claim 6 wherein separate scriber is provided with a carbide steel tip.

8. A measuring device as claimed in claim 1 wherein said model block is provided with a pair of mounting pins, and screw located therebetween for removably attaching a dental model to said model block.

9. A measuring device as claimed in claim 1 wherein said caliper is provided with a digital output and means for connecting the digital output of said caliper to a recording means.

10. In a measuring device for a dental model prior to orthognathic surgery and utilizing an anatomic dental articulator for mounting said dental model relative to the Frankfort Horizontal and for making measurements of a patient's jaws three planes in space, the improvement comprising: a model platform having a precisely flat top surface, an articulator block having means for supporting said dental articulator holding said dental model in an inverted position resting on the top surface of said model platform, and a vertically movable caliper mounted on and precisely at right angles to said platform and having means for accurately measuring said dental model.

11. A measuring device as claimed in claim 10 further comprising a scriber for placing reference lines on said dental model that have been measured by said caliper for facilitating prospective surgical procedures.

12. A measuring device for a dental model prior to orthognathic surgery comprising a model platform having a precisely flat platform surface, an occlusal block for making measurements from the occlusal plane, said occlusal block being rectangular in shape and provided with a dental compound on the top surface thereof, said dental model having a substantial number of teeth embedded thereon whereby said teeth are oriented with respect to said model platform as relates to said occlusal plane, and a vertically movable caliper mounted on and 90 degrees to said platform and having means for accurately measuring said dental model.

* * * * *